United States Patent [19]

Treuner

[11] Patent Number: 5,248,790
[45] Date of Patent: Sep. 28, 1993

[54] AMINOALKYLPHOSPHONIC ACID ESTERS OF NATURAL 4-METHOXY-5-METHYL-PYRAN-3-OL AND DERIVATIVES THEREOF

[75] Inventor: Uwe D. Treuner, Etterzhausen, Fed. Rep. of Germany

[73] Assignee: E. R. Squibb & Sons, Inc., Princeton, N.J.

[21] Appl. No.: 906,776

[22] Filed: Jun. 30, 1992

[51] Int. Cl.$^5$ .............................................. C09F 6/30
[52] U.S. Cl. .................................................... 549/222
[58] Field of Search ........................................ 549/222

[56] References Cited

U.S. PATENT DOCUMENTS 4,794,183 12/1988 Naka ..................................... 549/222
4,952,604 8/1990 Hensens et al. .

OTHER PUBLICATIONS

J. P. Van Wauwe et al., "Is There a Case for P-450 Inhibitors in Cancer Treatment?", Journal of Medicinal Chemistry, vol. 32, No. 10 (Oct. 1989), pp. 2231–2239.

R. E. Schwartz et al., "Restricticin, A Novel Glycine-Containing Antifungal Agent", Journal of Antibiotics, vol. 44, No. 5 (May 1991), pp. 463–471.

Primary Examiner—Marianne M. Cintins
Assistant Examiner—John Peabody
Attorney, Agent, or Firm—Ellen K. Park

[57] ABSTRACT

Antibiotic substances having the general formula

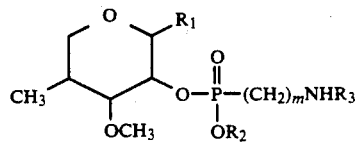

wherein $R_1$, $R_2$ and $R_3$ are as defined herein.

10 Claims, No Drawings

AMINOALKYLPHOSPHONIC ACID ESTERS OF NATURAL 4-METHOXY-5-METHYL-PYRAN-3-OL AND DERIVATIVES THEREOF

SUMMARY OF THE INVENTION

In accordance with the present invention, novel compounds having antibiotic and cytochrome P450 inhibition activity are disclosed. These compounds have the general formula $$\text{I}$$

and pharmaceutically acceptable salts thereof.

As used in formula I, and throughout the specification, the symbols have the following meanings:

$R_1$ is alkyl, alkenyl, arylalkyl, arylalkenyl, carboxy, $$-\overset{O}{\underset{\|}{C}}-R_4, \quad -\overset{R_{4'}}{\underset{|}{C}}=CH-\overset{O}{\underset{\|}{C}}-R_4, \quad -\overset{R_{4'}}{\underset{|}{C}}=CH-CH=CH-\overset{O}{\underset{\|}{C}}-R_4,$$

$$-\overset{OH}{\underset{|}{C}}R_4R_{4'} \quad \text{or} \quad -\overset{R_4}{\underset{|}{C}}=CH-CN;$$

$R_2$ is hydrogen or a lower alkyl $R_3$ is hydrogen or alkyl;

$R_4$ and $R_{4'}$ are independently hydrogen, alkyl or arylalkyl; and m is an integer of 1 to 4.

DETAILED DESCRIPTION OF THE INVENTION

Listed below are definitions of various terms used to describe the compounds of the instant invention. These definitions apply to the terms as they are used throughout the specification (unless they are otherwise limited in specific instances) either individually or as part of another group.

The term "alkyl" refers to both straight and branched chain hydrocarbons, containing 1 to 12 carbon atoms in the normal chain, preferably 1 to 5 carbon atoms as well as such groups optionally substituted with one or more substituents selected from halogen, alkyl, alkylthio, hydroxy, amino, alkylamino, dialkylamino, alkoxy, trifluoromethyl and carboxy. The term "lower alkyl" as employed herein includes such alkyl groups as described above containing 1 to 4 carbon atoms in the normal chain.

The term "alkenyl" refers to such groups as described above for alkyl, further containing at least one carbon to carbon double bond. Alkenyl groups having 5 to 10 carbon atoms in the normal chain are preferred.

The term "alkoxy" refers to such alkyl groups as described above, linked to an oxygen atom.

The term "aryl" refers to phenyl or phenyl substituted with halogen, alkyl, alkoxy, alkylthio, hydroxy, alkanoyl, nitro, amino, alkylamino, dialkylamino, cyano or trifluoromethyl groups. Phenyl and monosubstituted phenyl are preferred and phenyl is the most preferred.

The term "alkanoyl" refers to an alkyl group as described above, linked to a carbonyl group.

To prepare the compounds of formula I, where $R_2$ is a lower alkyl and $R_3$ is hydrogen, or a protected form thereof (where $R_2$ is replaced by a suitable protecting group ($R_x$) such as $-CH_2CH_2Si(CH_3)_3$ or $-CH_2CN$); an alcohol of the formula $$\text{II}$$

is reacted with an azide of the formula $$Cl_2-\overset{O}{\underset{\|}{P}}-(CH_2)_m-N_3 \quad \text{III}$$

in the presence of a base such as pyridine and in an aprotic solvent such as methylenechloride, to provide the intermediate products of formula $$\text{IV}$$

Compounds of formula IV, isolated or prior to isolation (in situ), can then be reacted with an alcohol such as methanol or ethanol, in the presence of a base such as pyridine or in the presence of an acid scavenger such as propyleneoxide or N,O-Bistrimethylsilylacetamide to form compounds of formula $$\text{V}$$

where $R_2$ is a lower alkyl or a protected form thereof (where $R_2$ is replaced by a suitable protecting group, $R_x$).

Compounds of formula V may then be treated with a reducing agent such as triethylphosphine and water or hydrogen sulfide/triethylamine to form the formula I compounds where $R_2$ is a lower alkyl and $R_3$ is hydrogen, or a protected form thereof where $R_2$ is replaced by a suitable protecting group, $R_x$.

Alternatively, compounds of formula V may be prepared by treating compounds of formula IV in water at a pH of from 5 to 7 preferably about 5.8 to form an intermediate of the formula $$\text{VI}$$

Formula VI compounds can then be reacted with a lower alkyl alcohol such as methanol or ethanol, in the presence of a coupling reagent suitable for phosphorous-ester bond formation such as a carbodiimide or a sulfonylimidazole to form the compounds of formula V.

Compounds of formula VI where $R_1$ is a saturated chain may also be reacted with hydrogen in the presence of a catalyst such as palladium on carbon to directly form compounds of formula I where $R_2$ and $R_3$ are hydrogen.

Compounds of formula I where $R_3$ is hydrogen, may also be prepared by reacting compounds of formula II with a compound of formula

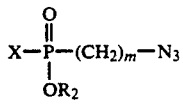
VII where X is chlorine, hydroxy or an activating group such as an anhydride mixed with a sulfonic acid, to form compounds of formula V which are then reduced using standard methodology.

Compounds of the formula I where $R_2$ is hydrogen are prepared from the protected forms of compounds of formula I where $R_2$ is replaced by a protecting group ($R_x$) by deprotection using known methods.

Compounds of formula I, where $R_1$ is alkyl or arylalkyl may also be prepared from compounds of formula V, where $R_1$ is an unsaturated side chain, by reducing the side chain by hydrogenation in the presence of a catalyst such as palladium on charcoal.

In the alternative, compounds of formula I may be prepared by reacting compounds of formula II with compounds of formula

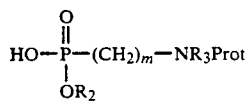
VIII to form compounds of formula

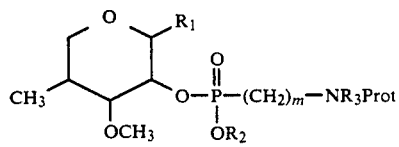
IX where Prot is a protecting group such as —COOC$_4$H$_9$ or —COOC$_2$H$_4$Si(CH$_3$)$_3$ which can then be deprotected to form compounds of formula I. In formulae VIII and IX, the substituent $R_2$ may also be replaced by $R_x$.

Intermediate compounds of the formula II where $R_1$ is alkyl, alkenyl, arylalkyl or arylalkenyl, may be prepared by treatment of the natural product scopularin (formula XA) and lanomycin (formula XB):

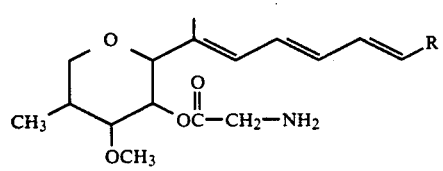

XA R = CH$_2$CH$_2$CH$_3$
XB R = CH$_3$ with a base such as sodium bicarbonate, in an organic solvent such as methanol to form the alcohol derivative of scopularin (formula XIA) or the alcohol derivative of lanomycin (formula XIB), respectively:

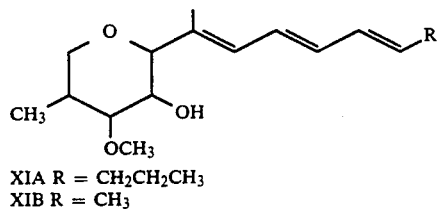

XIA R = CH$_2$CH$_2$CH$_3$
XIB R = CH$_3$

Standard methodologies can then be utilized to modify the $R_1$ side chains of the alcohols XIA or XIB as desired. For example, the $R_1$ side chain may be modified by reduction by subjecting compounds XIA or XIB to hydrogen gas in the presence of a catalyst such as palladium on carbon in an organic solvent such as methanol to provide partially hydrogenated intermediates or the totally hydrogenated intermediates XIIA and XIIB respectively:

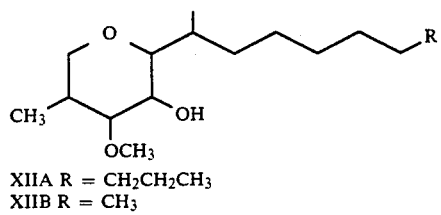

XIIA R = CH$_2$CH$_2$CH$_3$
XIIB R = CH$_3$

Compounds of formula II, where $R_1$ is other than alkyl or alkenyl (as exemplified by compounds of formulas XI A/B and XII A/B); may be prepared utilizing standard methodologies to degrade and modify the $R_1$ side chain of compounds of formula

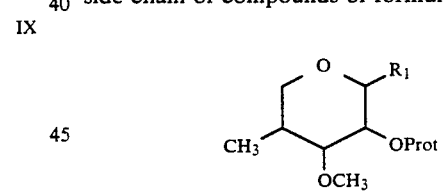
IIA where $R_1$ is the alkenyl side chain of compounds of formulas XIA or XIB and Prot is a protecting group such as —Si(CH$_3$)$_2$—R$_3$.

For example, treatment of compounds of formula IIA with an oxidating agent such as ozone at reduced temperatures in an organic solvent such as dichloromethane in the presence of a base such as pyridine provides compounds of formula IIA where $R_1$ is

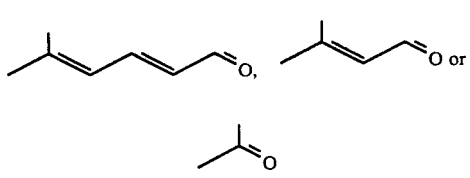

Further degradation of the compounds of formula IIA where the $R_1$ side chain is

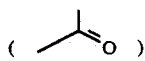

can be accomplished, for example, by treatment with a mixture of a steric hindered base such as lithium diisopropylamide, and a silylating agent such as t-butyldimethylsilylchloride, at reduced temperatures to provide the enolether of formula

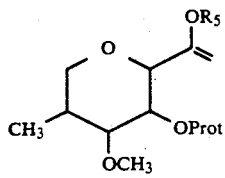

XIII where $R_5$ is hydrogen or a suitable protecting group such as $$-Si-C(CH_3)_3$$
$$\phantom{-Si-}|$$
$$\phantom{-Si}(CH_3)_2$$

or —$CH_2$-phenyl; which in turn can be reacted with a oxidizing agent such as ozone in an organic solvent such as dichloromethane in the presence of a base such as pyridine at reduced temperatures to provide the ester of formula

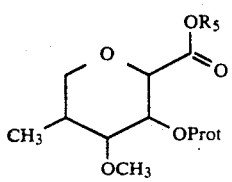

XIV or a protected form thereof, or after reductive work-up by treatment of the so-formed ester XIV with a reducing agent such as lithium aluminium hydride in an organic solvent such as tetrahydrofuran to provide the alcohol of formula

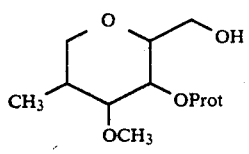

XV

A compound of formula XV can be further oxidized with an oxidizing agent such as oxalylchloride in the presence of dimethylsulfoxide and triethylamine at reduced temperatures to provide a compound of the formula

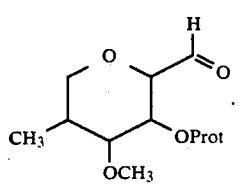

XVI

Compounds of the formula XVI and IIA (where $R_1$ is

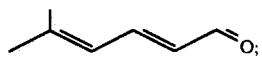
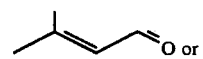
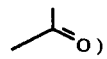

may be transformed by standard methodology such as Wittig-Horner, Horner-Emmons or Peterson-olefination reactions or Grignard-chain extension methods to prepare compounds of formula

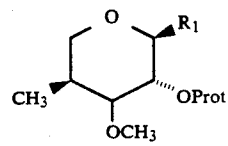

IIB where $R_1$ is alkenyl, arylalkyl or arylalkenyl, which can be deprotected to form a formula II compound.

The natural product of formulae XA and XB may be obtained by known methods, for example, as disclosed in copending U.S. patent application Ser. No. 723,292; filed June 28, 1991, incorporated herein by reference. The following is a description of one suitable method:

The Microorganism for Scopularin of Formula XA

The microorganism used for the production of scopularin is a strain of Scopulariopsis isolated from a soil sample collected from St. Paul's Gate, Rome, Italy. A subculture of the organism can be obtained from the American Type Culture Collection, Rockeville, Md. Its accession number in this repository is A.T.C.C. No. 20,914. In addition to the specific microorganism described and characterized herein, it should be understood that mutants of the microorganism produced through the use of chemical or physical mutagens can also be cultivated to produce the subject compound.

The microorganism can be isolated from a soil sample in which it is present by placing 0.5 gram of the soil in 10 ml of the following sterile buffer:

| | |
|---|---|
| NaCl | 8.5 g |
| $KH_2PO_4$ | 0.3 g |
| $Na_2HPO_4$ | 0.6 g |
| Gelatin | 0.1 g |
| Distilled Water to | 1000 ml |

The sample is mixed by vortexing and then sonicated for 10 minutes in an ultrasonic water bath. A series of dilutions are then prepared in the above buffer and 0.1 ml aliquots of the dilutions are spread-plated onto the following agar medium in order to obtain isolated colonies:

| | |
|---|---|
| Yeast extract | 2.0 g |
| Glucose | 5.0 g |
| Ocgall | 5.0 g |
| Sodium propionate | 1.0 g |
| $CaCO_3$ | 3.0 g |
| Agar | 2.0 g |
| V-8 Juice | 2 ml |
| Distilled Water | 800 ml |

-continued

| pH adjusted to 6.8 |

The medium is autoclaved at 121° C. for 15 minutes. Chlorotetracycline (30 mg/liter) and streptomycin (30 mg/liter) are added to the medium before dispensing into petri dishes.

After 5 days incubation at 25° C., colonies of Scopulariopsis sp. A.T.C.C. No. 20,914 are isolated from the plated samples. The isolated colonies are then grown on potato dextrose agar.

Colonies of Scopulariopsis sp. on potato-dextrose agar (PDA) grow rapidly with the leading edge of growth submerged in the agar. Surface growth from the center out is zonate with alternating bands of pinkish-buff to avellaneous (grey tinged with pink) in color. The reverse is brownish-orange with the center a deep burgundy red. The surface texture is lanose (wooly) with sporulation covering the agar plate. A deep burgundy exudate is produced on the aerial mycelium which upon drying produces craters giving the mycelial mat a pockmarked appearance.

On cornmeal agar growth of Scopulariopsis sp. is thin transparent and pinkish-grey in color. The reverse color is a mouse grey. Surface texture is lanose with droplets of colorless exudate clinging to aerial hyphae. With age the exudate becomes a burgundy red color tingeing the underlying agar. Heavy sporulation gives the culture a salt and pepper appearance. There is no evidence of formation of coremia or perithecia.

Hyphae of Scopulariopsis sp. are hyaline (colorless) when young, irregularly becoming fuscous (brownish-grey) with age. They are 1.5-2 μm in diameter. Sporulation occurs from the terminus of annellophores which are flask-shaped structures tapering to a narrow opening. Annellophores may occur singly or in verticils of 3-4 on the end of short hyphae. They average $4.5 \times 2$ μm in size.

The spores are produced within the annellophore by successive division of a mother nucleus and pass through this opening forming chains of varying length. Each successive spore formed leaves a characteristic scar on the outer wall of the annellophore. Spores are thick-walled with a truncate base occasionally with a small collarette attached. They are spherical to subovate, smooth and 3 μm in diameter. When first formed they appear smooth becoming rough with age. They have a longitudinal line which in fact is a thin-walled slit through which the germ tube passes at germination.

The following key diagnostic characters provide the basis for assigning the producing organism to the form-genus Scopulariopsis.

1. absence of coremia or perithecia;
2. annellidic sporulation;
3. presence of scars on the outer wall of the annellophore;
4. spore germination through a longitudinal germinal slit;
5. spores with truncate ends separated by a collarette;
6. spores borne in chains.

The Antibiotic Scopularin

The antibiotic scopularin can be produced by cultivating Scopulariopsis sp. A.T.C.C. No. 20,914 at, or near, 25° C. under submerged aerobic conditions in an aqueous nutrient medium containing assimilable carbohydrate and nitrogen sources. The fermentation is carried out until substantial activity is imparted to the medium, usually about 72 to 76 hours.

After three days the broths are pooled and filtered. The cell mass is extracted with methanol and the concentrated methanol extract is chromatographed on silica gel eluting with a methanol-chloroform step gradient. Final purification of the active fraction from the silica gel column is achieved using an Ito counter current chromatography coil with a heptane-ethyl acetate-methanol-buffer system.

Alternatively, the whole broth may be extracted with ethyl acetate and the concentrated organic phase partitioned in ethyl acetate/methanol/water (5:2:5). The activity partitions into the lower phase while most of the mass remains in the upper phase. After removal of the methanol in vacuo from the lower phase, the activity is re-extracted into ethyl acetate. The concentrated ethyl acetate layer is purified using the Ito and silica gel steps mentioned above.

The UV spectrum of scopularin, recorded in methanol, has an absorption maximum at 275 nm with an extinction coefficient of 37,000. Shoulders on the main band can be seen at 266 and 286 nm. There were no observable changes in the spectrum when recorded in acid or base. The Infra-red spectrum recorded in chloroform shows prominent bands are at 2970, 2940, 2860, 1740, 1460, 1390, 1115, 1030 and 990 cm$^{-1}$. The positive ion chemical ionization mass spectrum shows, that in addition to the pseudo-molecular ion at 338 daltons, other fragment ions can be observed at m/z 306, 263, 231, 202 and 170. A high resolution mass measurement of the [M+H]$^+$ ion in the Fast Atom Bombardment mass spectrum yielded a value of 338.2310. The exact mass calculated for the formula $C_{19}H_{32}NO_4$ is 338.2331. Other data such as 270 MHz proton spectrum recorded in deuteromethanol, 67.5 MHz carbon spectrum recorded in deuteromethanol and INEPT spectra may be found in the U.S. patent application Ser. No. 723,292 cited above.

Scopularin has a TLC $R_f$ of 0.4 when chromatographed on E. Merck Kieselgel 60 $F_{254}$ $5 \times 10$ cm plates using a chloroform/methanol (19:1) solvent system. An HPLC system consisting of a Varian 5020 LC, Spectra-Physics 4290 integrator, Perkin-Elmer CR $C_{18}$ $3 \times 3$ column, 1 mL/min. flow rate, with acetonitrile as the organic modifier and a 0.1M ammonium acetate (adjusted to pH 4.5 with acetic acid) buffer system, UV detection at 260 nm, was used. With a gradient composed of the following program of linear segments; T=0, 30% Organic, T=5 min., 50%, T=9.5 min., 100%, hold at 100% till 12 min. then back to 30% at 13 min., re-equilibrate at 30% for 3.5 min. between injections, scopularin has a retention time of approximately 6.6 min.

The Microorganism for Lanomycin of formula XB

The fungus is a strain of *Pycnidiophora dispersa* and was isolated from a soil sample collected in Culpepper, Va. A subculture of the organism can be obtained from the American Type Culture Collection, Rockeville, Md. Its accession number in this repository is A.T.C.C. No. 74,021. In addition to the specific microorganism described and characterized herein, it should be understood that mutants of the microorganism produced through the use of chemical or physical mutagens can also be cultivated to produce lanomycin and the alcohol thereof.

The microorganism can be isolated from a soil sample containing same by the procedures and media discussed above for Scopulariopsis Colonies of the fungus grew well on potato-dextrose agar and tomato juice agar. The sexual fruiting bodies (cleistothecia) were produced readily on these media but required 5 to 6 weeks for the ascospores borne within to mature. Cleistothecia were dark brown to black with an outer wall (peridium) composed of a single layer of polygonal pseudoparenchyma cells. Plates composed of radiating cells delineating lines of cleavage of the peridium were not evident. Cleistothecia occurred singly or in clusters but each had its own peridium.

Sac-like asci were produced from fertile hyphae randomly distributed within the lumen of the cleistothecium. Histological examination of thin sections of the ascus cell wall showed it to be unitunicate. Each ascus bore ascospores in multiples of eight depending on the stage of division. The ascospores were elliptical, pigmented and partially septate with an oil globule at each end. They were not bivalve and did not possess a longitudinal germinal slit. They germinated by means of a terminal or lateral germ tube. Ascospores were $4.7 \times 2.5$ u. Paraphyses, specialized filiform cells interspersed among the asci, were lacking.

The asexual cycle consisted of pycnidia which were ovoid bodies with an ostiole or pore. Conidia were borne on short conidiophores which lined the inner layer of the pycnidium. When the central cavity of the pycnidium was filled with spores, they were released through the ostiole in a slime. Conidia were elliptical, smooth, hyaline and averaged $3 \times 2$ u in size. Monoconidial isolates produced cultures which fruited both sexually and asexually, as, indeed, did monoascospore cultures. This agreed with the original observation by Clum (1955) which formed the basis for the identification of Pycnidiophora. This organism is a member of a well-known group of Ascomycetes some of which were discovered as early as 1866. There has been and continues to be considerable controversy as to their taxonomic placement, specifically at the ordinal and family levels. When our isolate, SC15017 was directly compared with the type culture of *Pycnidiophora dispersa* (Clum, 1955) they were found to be identical. The description also matches that of the organism reported in the Japanese Patent 18952 in which the name *Westerdykella dispersa* was used; that assignment was based on their comparison with *W. dispersa* IFO strain 8431, however, the IFO strain was not the original Clum strain. These organisms all share the following characteristics:

1) the sexual fruiting body is a true cleistothecium with a discrete peridium;
2) The asci have a single layered wall;
3) the ascospores are free with up to 32 per ascus rather than disarticulated segments of eight 4-celled ascospores;
4) the asexual stage is pycnidial.

The data presented here forms the basis for the identification of SC15017 as *Pycnidiophora dispersa* sensu Clum (1955) and the designation of *Westerdykella dispersa* as a synonym. *Pycnidiophora dispersa* (Clum) is recognized by Thompson & Backus (1966) and supported by Mukerji & Saksena (1975).

The Antibiotic Lanomycin

The antibiotic lanomycin can be produced by cultivating *Pycnidiophora dispersa*, A.T.C.C. No. 74,021 at, or near, 25° C. under submerged aerobic conditions in an aqueous nutrient medium containing assimilable carbohydrate and nitrogen sources. The fermentation is carried out until substantial activity is imparted to the medium, usually about 72 to 76 hours.

After three days the broths are pooled and filtered. The cell mass is extracted with ethyl acetate and the concentrated ethyl acetate extract is chromatographed on silica gel eluting with a heptane-ethyl acetate-methanol step gradient. Final purification of the active fractions from the silica gel column is achieved using an Ito counter current chromatography oil with a heptane-chloroform-methanol buffer system.

Compounds of formula III may be prepared by standard procedures as described generally in Houben-Wey "Methodem der organ.Chemie" Vol XII. One example of the preparation of a compound of formula III, where (m=1), is to react a compound of the formula

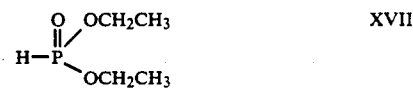

XVII with paraformaldehyde in the presence of a base such as triethylamine to form a compound having the formula

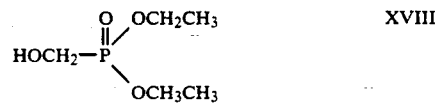

XVIII which is then reacted with a leaving group forming reagent such as pTosCl and a base such as dimethylaminopyridine in an aprotic solvent such as dimethylformamide to form a compound of the formula

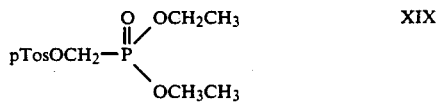

XIX

A compound of formula XIX is then reacted with an azide such as NaN₃ in an organic solvent such as dimethylformamide to form a compound of formula

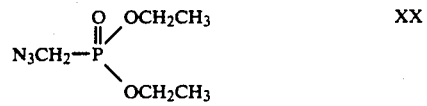

XX which is then reacted with an alkylsilylhalide such as trimethylsilylbromide and then with a P—Cl bond forming reagent such as (COCl)₂ to form compounds of formula III where m=1. Compounds of formula III where m is other than the integer 1 are prepared by known methods or are commercially available.

Compounds of the formula VII and VIII may be prepared by conventional methods or are commercially available.

Preparation of intermediates of formulae IIA, XIIA, XIIB, XIII, XIV, XV and XVI are also described in the U.S. patent application, Ser. No. 723,292 cited above.

All stereochemical isomers (diastereomers and enantiomers) as well as all geometrical isomers (E,Z-isomers) of compounds of formula I are within the scope of the invention. Preferred compounds are those of the formula

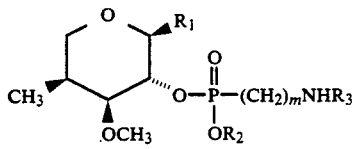

wherein $R_1$ is alkyl, alkenyl or arylalkenyl and $R_2$ is hydrogen, methyl or ethyl. Most preferred are those compounds of formula I' where m is the integer 1; $R_1$ is selected from

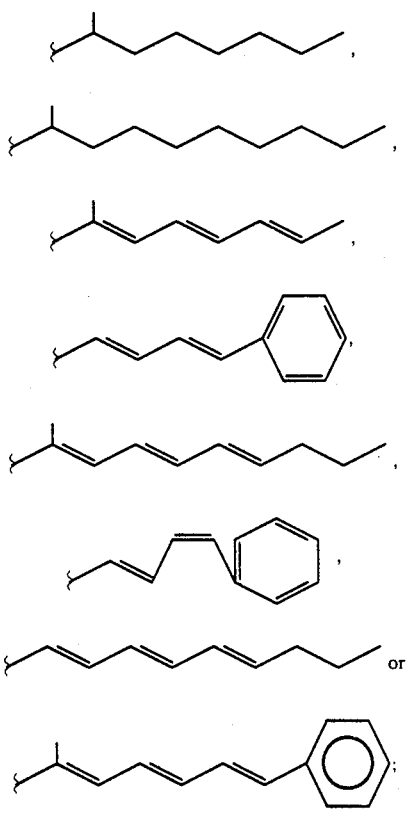

$R_2$ is hydrogen, methyl or ethyl and $R_3$ is hydrogen.

The compounds of formula I and pharmaceutically acceptable salts thereof, can be used to combat fungal infections (particularly infections of Candida and other yeasts and filamentous fungi, such as Tricophyton, Microsporum, etc.) in domesticated animals and humans. In addition, these compounds have been found to inhibit cytochrome P450 enzymes, such as lanosterol demethylase. These compounds can therefore be used in a variety of ways including as an adrenal steroidogenesis inhibitor against infections caused by protozoa for the treatment of metastatic mammary carcinoma, in postmenopausal or ovariectomized women, in Cushing's syndrome, in breast, prostatic, endometrial, ovarian and pancreatic carcinomas, and as an inhibitor of aromatase or other cytochrome P450 enzymes. Based on this cytochrome P450 inhibition activity, the compounds of the present invention are also expected to be useful in the treatment of hypertension. These compounds can be administered topically, orally or parenterally. The dosage used of the compounds of formula I, a pharmaceutically acceptable salt thereof will vary with the severity of the infection or disorder and the size of the host. For a human adult, daily doses of about 100 mg to 1 gm/day are exemplary.

Compounds of formula I, or salts thereof, may also be used in the treatment of fungal diseases of plants and may be used as plant growth regulators by inhibition of cytochrome P450 monooxygenases involved in the biosynthesis of gibberellin. Treatment with the compounds of formula I for these uses may be carried out by application to seed, foliage or to the soil.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

Scopulariopsis sp. A.T.C.C. No. 20,914 was maintained on the following sterilized agar medium (A):

| | |
|---|---|
| Malt Extract | 10.0 g |
| Yeast Extract | 10.0 g |
| Peptone | 1.0 g |
| Dextrose | 20.0 g |
| Agar | 15.0 g |
| Distilled Water to | 1000 ml |
| The pH was adjusted to 7.0 and the medium was sterilized at 121° C. for 20 minutes. | |

A loopful of surface growth from agar slants (Medium A) of Scopulariopsis sp. was used to inoculate each of five 500 ml Erlenmeyer flasks each containing 100 ml of the following sterilized medium (B):

| | |
|---|---|
| Toasted Nutrisoy Flour | 15.0 g |
| Soluble Starch | 15.0 g |
| Glucose | 50.0 g |
| $CoCl_2.6H_2O$ | 0.005 g |
| $CaCO_3$ | 10.0 g |
| Distilled Water to | 1000 ml |

After inoculation, the flasks were incubated at 25° C. on a rotary shaker (300 rpm; 2 inch stroke) for approximately 72 hours with a resulting broth pH 6.0–6.5. Transfers of 4% (vol./vol.) were made from the grown culture flasks to one hundred 500 ml Erlenmeyer flasks each containing 100 ml of sterilized medium C: (Medium C was Medium A described above without the addition of agar). After inoculation, the flasks were once again incubated at 25° C. on a rotary shaker (as previously described) for approximately 72 hours with a resulting broth pH of 6.0–6.5. At this time, the contents of the flasks were pooled and the broth was filtered. The cell mass (2.0 kg) obtained was extracted twice with 2 L portions of methanol (1 hour for each extraction) and the extract concentrate (ca. 4.5 X) was isolated.

Examples 2 and 3, which follow, outline typical isolation techniques used for isolation of Scopularin after fermentation as described above.

EXAMPLE 2

After the fermentation was completed, the pooled whole broth was filtered and the cell cake, consisting of 500 mL of wet cells, was extracted with 2×1 L portions of methanol, stirring the suspension for one hour with each pass. The combined methanol extracts were concentrated to 100 mL and this aqueous residue was lyophilized. The resulting oil was redissolved in a minimum of methanol and applied to the head of a 2.5×15 cm column packed with Merck silica gel and equilibrated with heptane. The column was eluted with 2 L of ethyl acetate/heptane (1:9) followed by 1 L portions of methanol/chloroform (1:200) followed by (1:100) followed by (1:50). Twenty five mL fractions were collected and assayed by TLC. (TLC $R_f$ of 0.4 on E. Merck Kieselgel 60 $F_{254}$ 5×10 cm plates with a methanol/chloroform (1:19) solvent system). Fractions containing Scopularin by TLC were pooled and the solvent removed. The active fraction from the silica gel column was loaded onto the head of an Ito Multi-Layer Coil Separator-Extractor (P. C. Inc., Potomac, Md.) which was filled with the lower phase of a heptane/ethyl acetate/methanol/buffer (0.1M ammonium acetate adjusted to pH 4.5 with acetic acid) (1:1:1:1) system. The coil, a multilayer teflon tubing (1.6 mm, i.d.) with a volume of 330 mL, was spun at 800 rpm and the upper phase of the solvent system was pumped through the coil at 4 mL/min. and collected in 5 minute fractions. Pure scopularin eluted in fractions 32–46. These fractions were pooled and the solvent evaporated to yield 15 mg of pure $(2\alpha, 3\beta, 4\alpha, 5\alpha)$-Tetrahydro-4-methoxy-5-methyl-2-(1-methyl-1,3,5-nonatrienyl)-2H-pyran-3-ol, amino-acetate ester.

EXAMPLE 3

The pooled whole broth from a 10 L fermentation was extracted with 2, five L portions of ethyl acetate and the combined organic layers were concentrated to an oil and taken up in a small volume of methanol for storage in a freezer. The extracts from five 10 L batches were pooled and concentrated to an oily residue and this residue re-dissolved in 100 mL methanol. Fifty mL of the pooled extract was shaken with an additional 50 mL methanol and 250 mL ethyl acetate and 250 mL water. After removal of the aqueous layer, the organic phase was re-extracted with two additional 250 mL portions of lower phase from the ethyl acetate/methanol/water (5:2:5) solvent mixture. The combined aqueous phases were concentrated to approximately 100 mL in vacuo and extracted with 3×100 mL portions of ethyl acetate. The combined ethyl acetate phases were concentrated to dryness. The above extraction procedure was performed on the remaining 50 mL of methanol concentrate and the final ethyl acetate concentrates were combined. This material was purified using the Ito and silica gel steps as given above to yield 70 mg pure scopularin.

The following example illustrates synthesis of the alcohol derivative of scopularin. A similar process may be employed to produce the alcohol derivative of lanomycin.

EXAMPLE 4

Alcohol Derivative of Scopularin4

The alcohol of scopularin is easily prepared from scopularin by basic hydrolysis of its ester linkage. For example, 60 mg of scopularin was dissolved in 2 mL methanol. 1 mL of saturated, sodium carbonate solution was added and the mixture was allowed to stir. After 2 hours the reaction was complete as judged by TLC. (The alcohol has an $R_f$ of 0.4 on Merck silica gel plates, using ethyl acetate/heptane (2:3) as the developing solvent, and may be visualized using short wave ultraviolet light, $I_2$, phosphomolybdic acid, vanillin/$H_2SO_4$, and other reagents sensitive to olefins and hydroxyl groups.) The mixture was diluted with 20 mL $H_2O$ and the resulting solution was extracted three times with 50 mL portions of dichloromethane. The combined organic extracts were dried over sodium sulfate, concentrated and chromatographed on a 20 g silica gel column using ethyl acetate/heptane (15:85) as the eluting solvent. Five mL fractions were collected and examined by TLC. Fractions containing pure alcohol were pooled and the solvent evaporated to yield 40 mg, 80% of the theoretical yield of scopularin alcohol.

EXAMPLE 5

*Pycnidiophora dispersa*, A.T.C.C. No. 74,021 was maintained on the following sterilized agar medium:

| Medium A | |
| --- | --- |
| Malt Extract | 10.0 g |
| Yeast Extract | 10.0 g |
| Peptone | 1.0 g |
| Dextrose | 20.0 g |
| Agar | 15.0 g |
| Distilled Water to | 1000 ml |
| The pH was adjusted to 7.0 and the medium was sterilized at 121° C. for 20 minutes. | |

Seed cultures were prepared by transferring a loopful of surface growth from an agar slant culture of *P. dispersa* SC15017 (A.T.C.C. 74,021) into 500 ml Erlenmeyer flasks containing 100 ml of sterilized medium. The medium contained toasted nutrisoy flour, 1.5%, soluble starch, 1.5%, glucose, 5%, $CoCl_2.6H_2O$, 0.0005%, $CaCO_3$, 1% and distilled water. Inoculated flasks were incubated at 25° C. on a rotary shaker (300 rpm; 5 cm stroke) for approximately 72 hours. A 5% transfer of this culture was then made to Erlenmeyer flasks each containing 100 ml of the following medium: glucose, 2.5%, yeast extract, 0.2%, N-Z amine A, 0.4%, $K_2HPO_4$, 0.1%, $NaH_2PO_4.H_2O$, 0.1%, $NH_4Cl$, 0.05%, $MgSO_4.7H_2O$, 0.02% and distilled water. The pH was adjusted to 7. Flasks were incubated at 25° C. on a rotary shaker at 300 rpm as before. At about 48 hours flasks were harvested by filtration through celite.

The following example outlines the typical isolation technique for isolation of lanomycin after fermentation as described above.

EXAMPLE 6

Isolation of Lanomycin

The culture beer (10 L fermentation) was filtered and the cells discarded. The filtrate was extracted twice with ½ volumes of ethyl acetate. The combined organic layers were concentrated to give 1.40 g of a brownish oil. This sample was split and 700 mg subjected to countercurrent chromatography in heptane-ethyl acetate-methanol—pH 4.5, 0.1M $NH_4OAc$ buffer (1:2:1:2), organic phase mobile using a high-speed countercurrent chromatograph, (P. C. Inc., Potomac, Md., U.S.A.) operated at 800 rpm using a 330 ml volume multilayer Teflon tube (1.6 mm i.d.). This yielded lanomycin, 100 mg, sufficiently pure for spectroscopy and chemical degradation. The second compound was not recovered from this purification, however, and in subsequent workups, the oil was first chromatographed on a 3.0×25 cm bed of silica gel eluted with increasing concentrations of methanol in chloroform to give a fraction containing mostly lanomycin. Lanomycin was then purified using the Ito coil as described above.

Lanomycin

2α,3β,4α,5α)-Tetrahydro-4-methoxy-5-methyl-2-(1-methyl-1,3,5-heptatrienyl)-2H-pyran-3-ol, amino-acetate ester. Slightly yellow oil, $[\alpha]_D + °(c, MeOH)$; TLC (CHCl$_3$—CH$_3$OH, 19:1) R$_f$ 0.45; UV in CH$_3$OH, $\lambda_{max}$ (logε), 266(4.25) 273(4.37), 284(4.27), IR (CHCl$_3$) cm$^{-1}$, 2960, 2920, 2840, 1735, 1700, 1610, 1440, 1380, 1110, 1025, 980. MS/HRMS, positive ion CI{CH$_4$/N$_2$O}, m/z. HRFAB vs. PEG 310 [M+H]+, 270, 253, 235, 203. Measured 310.2025; C$_{17}$H$_{28}$NO$_4$=310.2018.

EXAMPLE 7

(Aminomethyl)phosphonic acid, methyl [2S-[2α(E,E,E), 3β,4α,5α]]-tetrahydro-4-methoxy-5-methyl-2-(1-methyl-1,3,5-heptatrienyl]-2H-pyran-3-yl ester,isomer A A.
(2α,3β,4α,5α)-Tetrahydro-4-methoxy-5-methyl-2-(1-methyl-1,3,5-heptatrienyl)-2H-3ol The sample (680 mg) of the ethyl acetate extract concentrate from an alkaline (pH 8) fermentation filtrate (from Example 5), was loaded in 3 mL of chloroform onto the head of a 100 g silicon oxide column (bed volume 25×450 mm) which had been equilibrated with 0.75% methanol/chloroform. After loading flow of 0.75% methanol/chloroform was maintained at 4 mL/minute and 5 mL fractions were collected. Fractions 66 through 69 contained the title compound. These fractions were pooled and the solvent evaporated to yield 20 mg of the pure alcohol.

B. (Azidomethyl)phosphonic acid, methyl [2S-[2α-(E,E,E),3β,4α,5α]]-tetrahydro-4-methoxy-5-methyl-2-(1-methyl-1,3,5-heptatrienyl)-2H-pyran-3-yl ester, isomer A 1. (Hydroxymethyl)phosphinic acid, diethyl ester Phosphinic acid, diethyl ester (140 g) and paraformaldehyde (30 g) were mixed and triethylamine (5 g) was added. The temperature of the exothermic reaction was kept at 70° C. by cooling with water. After 20 minutes the cooling bath was removed and the temperature of the reaction solution was allowed to slow down to room temperature. After 1 hour stirring fractioned distillation gave the title compound (153.4 g) as a colorless oil: B$_p$: 118-124° C.

2. [[[(4-Methylphenyl)sulfonyl]oxy]methyl]-phosphinic acid, diethyl ester

To the title 1 compound (17 g) and 4-dimethylaminopyridine (12 g) dissolved in tetrahydrofuran (100 mL) at −28° C. a solution of p-toluenesulfonic acid chloride in tetrahydrofuran (100 mL) was added dropwise. Stirring was continued overnight at room temperature. The solvent was distilled off and the residue was dissolved in 300 mL ether/ice water. The organic phase was washed with a 10% citric acid solution in water, with brine and dried over magnesium sulfate. Evaporation gave the title compound as a colorless oil (33.9 g).

3. (Azidomethyl)phosphinic acid, diethyl ester

The title 2 compound (11 g) was dissolved in dimethylformamide (50 mL). Sodium azide (3.5 g), KJ (0.1 g) and C-18-crown 6 (0.1 ng) were added. The mixture was stirred at 70° C. for 3 hours. The dimethylformamide was distilled off and the residue dissolved in ether/water. The organic phase was washed with water and brine, dried over magnesium sulfate and evaporated. Distillation of the oily residue yielded the title compound (5.45 g) as a colorless oil. B$_p$: 71-76° C.

4. (Azidomethyl)phosphinic acid, bis trimethylsilyl) ester

The title 3 compound (3.2 g) was dissolved in methylene chloride (20 mL) and trimethylsilylbromide (6.2 mL) was added. After stirring for 2 hours at room temperature, the solvent and the formed ethylbromide were distilled off. The title compound (4.66 g), a yellowish oil residue was obtained.

5. (Azidomethyl)phosphinic dichloride

The title 4 compound (4.5 g) oxalylchloride (2.5 mL) and methylene chloride (5 mL) were stirred at −10° C. for two hours and then overnight at room temperature. Evaporation and distillation gave the title compound (2.78 g).

6. (Azidomethyl)phosphonic acid, methyl [2S-[2α-(E,E,E),3β,4α,5α]]-tetrahydro-4-methoxy-5-methyl-2-(1-methyl-1,3,5-heptatrienyl)-2H-pyran-3-yl ester To the title A compound (1 g) in methylene chloride (50 mL) was added pyridine (330 µL) and the title 5 compound (0.7 g). After nine hours stirring at room temperature, methanol (5 mL) was added and stirring continued for 15 minutes at −40° C. After distilling off the solvents the residue was treated with water/ethyl acetate. The organic phase washed with brine and dried over magnesium sulfate. Evaporation gave an oily residue of the title compound (isomers A and B) together with small amounts of educt of the title A compound. Purification and separation of the isomers: CC on silica gel diisopropylether/tert-butylmethyl-ether (6:4) as eluent gave: 850 mg isomer B (R$_f$0.44) [HI=89%] 970 mg isomer A, the title compound (R$_f$0.31) [HI=89%] and 218 mg educt. 2 CC of the title compound=370 mg=31% [HI=92%].

C. (Aminomethyl)phosphonic acid, methyl [2S-[2α(E,E,E),3β,4α,5α]]-tetrahydro-4-methoxy-5-methyl-2-(1-methyl-1,3,5-heptatrienyl)-2H-pyran-3-yl ester,isomer A To the title B compound (370 mg; isomer A) in tetrahydrofuran (5 mL) was added triethylphosphine 160 µl at −50° C. After stirring for 30 minutes at that temperature and an additional four hours at room temperature two eq. water were added and stirring was continued overnight. Evaporation and CC of the oily residue on silicon dioxide tetrahydrofuran as eluent for the first two CC runs and methanol/acetonitrile (2:8) for the third purification yielded the title compound (117 mg) as an oil [HI=99.7%]; and 70 mg [HI=94%].

EXAMPLE 8

(Aminomethyl)phosphonic acid, [2S-[2α(E,E,E), 3β,4α,5α]-tetrahydro-4-methoxy-5-methyl-2-(1-methyl-1,3,5-heptatrienyl)-2H-pyran-3-yl 2-(trimethylsilyl)ethyl ester, isomer A A. (Azidomethyl)phosphonic acid, [2S-[2α(E,E,E), 3β,4α,5α]]-tetrahydro-4-methoxy-5-methyl-2-(1-methyl-1,3,5-heptatrienyl)-2H-pyran-3-yl ester To the title A compound of Example 7 (480 mg) dissolved in methylene chloride (170 mL) and pyridine (170 μL) was added dropwise (azidomethyl)phosphinic dichloride (500 mg; the title 5 compound from Example 1) while stirring at room temperature. After five hours the reaction was completed (DC). Water was added and the pH was adjusted with sodium bicarbonate to 5.0. After overnight stirring, the solution was extracted with methylene chloride. Evaporation of the organic phase resulted in the crude title compound (530 mg; HI 89.7%).

B. (Azidomethyl phosphonic acid, [2S-[2α(E,E,E), 3β,4α,5α]]-tetrahydro-4-methoxy-5-methyl-2-(1-methyl-1,3,5-heptatrienyl)-2H-pyran-3-yl-2-(trimethylsilyl)ethyl ester The title A compound (800 mg), 2-(trimethylsilyl)-ethanol (900 mg) and WSCD (watersoluble carbodiimide; 1.3 g) were stirred in methylene chloride (50 mL) for 12 hours. Extraction with water, drying the organic phase and its evaporation yielded crude title compound (1.23 g) as a diastereomeric mixture. Purification by CC (silicon dioxide; eluent diisopropylether/diethylether 7:3) yielded 1.08 g unresolved diastereomeric mixture.

C. (Aminomethyl)phosphonic acid, [2S-2α (E,E,E), 3β,4α,5α]]-tetrahydro-4-methoxy-5-methyl-2-(1-methyl-1,3,5-heptatrienyl)-2H-pyran-3-yl-2(trimethylsilyl)ethyl ester, isomer A To the title B compound (1.08 g) in tetrahydrofuran (50 mL) was added triethylphosphine (0.57 g) at −40° C. The cooling bath was removed and the reaction solution stirred for three hours. Water (0.5 mL) was then added and stirring continued for 24 hours. Evaporation and SC of the residue on silicon dioxide tetrahydrofuran as solvent yielded the title compound (484 mg; Isomer A: 484 mg, R$_f$ 0.78; and Isomer B: 249 mg, R$_f$ 0.5). The title compound was crystallized from n-hexane Mp. 54° C.

EXAMPLE 9

(Aminomethyl)phosphonic acid, methyl [2S-[2α(E,E,E), 3β,4α,5α]]-tetrahydro-4-methoxy-5-methyl-2-(1-methyl-1,3,5-heptatrienyl)-2H-pyran-3-yl ester, isomer B Isomer B (254 mg) of the title B.6 compound of Example 7 ((Azidomethyl)phosphonic acid, methyl [2S-[2α-(E,E,E),3β,4α,5α]]-tetrahydro-4-methoxy-5-methyl-2-(1-methyl-1,3,5-heptatrienyl)-2H-pyran-3-yl ester) was dissolved in tetrahydrofuran (7 mL) under Argon at −30° C. and triethylphosphine (195 μl) was added. After 30 minutes the temperature was allowed to come to room temperature. Stirring was continued for four hours. After that time water (2 mL) was added and stirring continued for 12 hours. After stripping off the solvent n vacuo the oily residue was purified by CC on silicon dioxide—RP8B water/acetonitrile as eluent.

The title compound (100 mg; HI=98%) was obtained as an oil.

EXAMPLE 10

(Aminomethyl)phosphonic acid, [2S-[2α(E,E,E),-3β,4α,5α]]-tetrahydro-4-methoxy-5-methyl-2-(1-methyl-1,3,5-heptatrienyl)-2H-pyran-3-yl ester To the title A compound of Example 8 (265 mg) dissolved in dimethylformamide (30 mL) was added cesium fluoride (250 mg). After stirring for 36 hours under inert gas at room temperature, excess cesium fluoride was filtered off (150 mg). The dimethylformamide of the filtrate was distilled off in vacuo and the residue stirred with ether (10 mL). A light yellow solid was formed which was isolated and redissolved in methylene chloride (20 mL , filtered (15 mg ↓ cesium fluoride) and the filtrate evaporated yielding the crude cesium-salt of the title compound 190 mg; HI=76%). This material was further purified by preparative HPLC on PLRPS, acetonitrile/water [18/72] pH 3.2 (acetic acid) as eluent yielding the title compound as a white solid (64 mg after freeze drying; HI=91.2%).

EXAMPLE 11

(Aminomethyl)phosphonic acid, [2S-[2α-(E,E,E), 3β,4α,5α]]-tetrahydro-4-methoxy-5-methyl-2-(1-methyl-1,3,5-heptatrienyl)-2H-pyran-3-yl ester A. (Azidomethyl)phosphonic acid, [2S-[2α-(E,E,E), 3β,4α,5α]]-tetrahydro-4-methoxy-5-methyl-2-(1-methyl-1,3,5-heptatrienyl)-2H-pyran-3-yl ester To the title A compound of Example 7 (480 mg) dissolved in methylene chloride (170 mL) and pyridine (170 μL) was added dropwise (azidomethyl)phosphinic dichloride (500 mg; the title B.5 compound of Example 7) while stirring at room temperature. After five hours the reaction was completed (DC). Water was added and the pH adjusted with sodium bicarbonate to 5.0. After overnight stirring, the solution was extracted with methylene chloride. Evaporation of the organic phase resulted in the crude title compound as a white solid (530 mg; HI=89.7).

B. (Aminomethyl)phosphonic acid, [2S-[2α-(E,E,E), 3β,4α,5α]]-tetrahydro-4-methoxy-5-methyl-2-(1-methyl-1,3,5-heptatrienyl)-2H-pyran-3-yl ester The crude title A compound (150 mg; HI=90%) was dissolved in methylene chloride (2 mL) and triethylamine (2 mL). Hydrogen sulfide gas was bubbled for one hour through the solution. After continuous stirring for three hours solvent and excess triethylamine were distilled off. The residue was suspended in water/acetonitrile (5 mL; 85:15) and after one minute ultrasound treatment, the residue was filtered. The filtrate was subjected to a CC run on PLRPR-S (30% acetonitrile/water). Relevant fractions, after freeze drying gave the title compound as the triethylamine salt (152 mg).

EXAMPLE 12

(Azidomethyl)phosphonic acid, ethyl [2S-[2α-(E,E,E)-3β,4α]]-tetrahydro-4-methoxy-5-methyl-2-(1-methyl-1,3,5-heptatrienyl)-2H-pyran-3-yl ester, isomer A and isomer B The title A compound of Example 7 (1 g) and pyridine (400 μL) were dissolved in methylene chloride (40 mL). The title B.5 compound of Example 7 (1.1 g) was added dropwise and after continuous stirring for five hours at room temperature, ethanol (10 mL) was added and stirring continued overnight. After keeping the reaction solution at 50° C. for 30 minutes, the solution was cooled down and extracted with phosphate buffer (pH 5) and water. From the dried and evaporated organic phase the crude title compound together with its diastereomer "isomer B" was obtained as a colorless oil (1.54 g). Purification by CC on silicon dioxide diisopropylether/diethylether (7:3) yielded the mixture of isomers A and B (1.41 g). The diastereoisomers of the title compound were cleanly separated by a second CC on silicon dioxide diisopropylether/methanol (8.2:1.8) yielding the title compound isomer A ($R_f$ 0 26; 0.641 g) and isomer B ($R_f$ 0.32; 0.665 g). Both compounds are oils.

EXAMPLE 13

(Aminomethyl)phosphonic acid, ethyl[2S-[2α(E,E,E), 3β,4α,5α]]-tetrahydro-4-methoxy-5-methyl-2-(1-methyl-1,3,5-heptatrieny)-2H-pyran-3-yl ester, isomer A To the title compound of Example 12 (isomer A; 0.440 g) in tetrahydrofuran (30 mL) was added triethylphosphine (0.57 g) at −40° C. The reaction solution was allowed to reach room temperature while stirring. After three hours water (0.5 mL) was added and stirring continued overnight. The only residue obtained after evaporation was purified by CC on silicon dioxide tetrahydrofuran as an eluent, yielding the title compound $R_f$=0 72; HI=90.8% (0.353 g).

EXAMPLE 14

(Aminomethyl)phosphonic acid, ethyl[2S-[2α(E,E,E), 3β,4α,5α]]-tetrahydro-4-methoxy-5-methyl-2-(1-methyl-1,3,5-heptatrienyl)-2H-pyran-3-yl ester, isomer B The title compound of Example 12 (isomer B; 0.4 g) was reduced with triethylphosphine analog (Example 13). The title compound (0.34 g) was obtained as an oil. $R_f$=0.26; HI=93.5%.

What is claimed is:

1. A compound of the formula

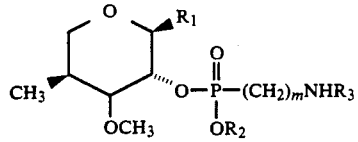

I or a pharmaceutically acceptable salt thereof:
where $R_1$ is alkyl, alkenyl, arylalkyl, arylalkenyl, carboxy,

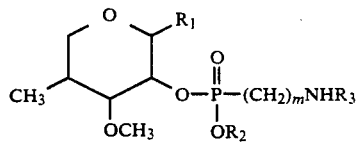

$R_2$ is hydrogen or a lower alkyl;
$R_3$ is hydrogen or alkyl;
$R_4$ and $R_4'$ are independently hydrogen, alkyl or arylalkyl; and
m is an integer of 1 to 4.

2. A compound of claim 1 having the structure

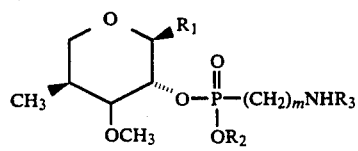

I' wherein $R_1$ is alkyl, alkenyl or arylalkenyl and $R_2$ is hydrogen, methyl or ethyl.

3. A compound of claim 1 having the structure

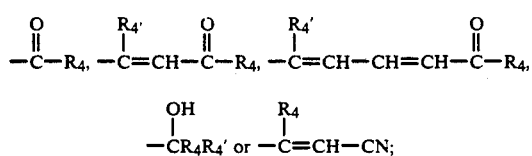

I' wherein m is the integer 1; $R_1$ is selected from

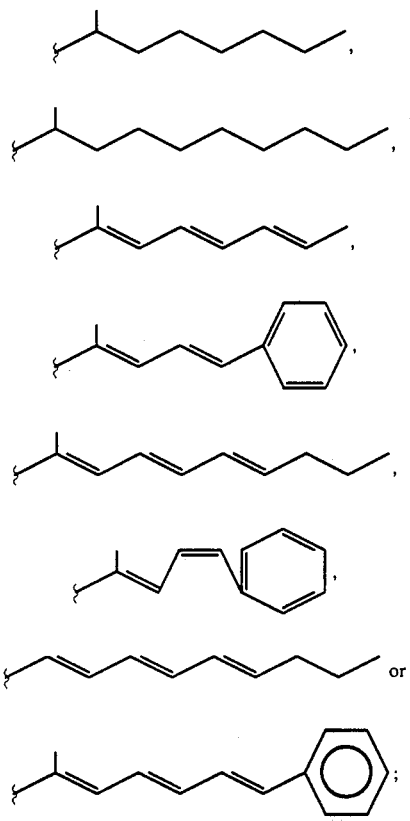

$R_2$ is hydrogen, methyl or ethyl and $R_3$ is hydrogen.

4. A compound of claim 1, (Aminomethyl)phosphonic acid, methyl [2S-[2α(E,E,E),3β,4α,5α]]-tetrahydro-4-methoxy-5-methyl-2-(1-methyl-1,3,5-heptatrienyl)-2H-pyran-3-yl ester, isomer A, or a pharmaceutically acceptable salt thereof.

5. A compound of claim 1, (Aminomethyl)phosphonic acid, [2S-[2α(E,E,E),3β,4α,5α]]-tetrahydro-4-methoxy-5-methyl-2-(1-methyl-1,3,5-heptatrienyl)-2H-pyran-3-yl 2-(trimethylsilyl)ethyl ester, isomer A, or a pharmaceutically acceptable salt thereof.

6. A compound of claim 1, (Aminomethyl)phosphonic acid, methyl [2S-[2α(E,E,E),3β,4α,5α]]-tetrahydro-4-methoxy-5-methyl-2-(1-methyl-2H-pyran-3-yl ester, isomer B, or a pharmaceutically acceptable salt thereof.

7. A compound of claim 1, (Aminomethyl)phosphonic acid, [2S-[2α(E,E,E),3β,4α,5α]]-tetrahydro-4-methoxy-5-methyl-2-(1-methyl-1,3,5-heptatrienyl)-2H-pyran-3-yl ester, or a pharmaceutically acceptable salt thereof.

8. A compound of claim 1, (Aminomethyl)phosphonic acid, [2S-[2α-(E,E,E), 3β,4α,5α]]-tetrahydro-4-methoxy-5-methyl-2-(1-methyl-1,3,5-heptatrienyl)-2H-pyran-3-yl ester, or a pharmaceutically acceptable salt thereof.

9. A compound of claim 1, (Aminomethyl)phosphonic acid, ethyl[2S-[2α-(E,E,E), 3β,4α,5α]]-tetrahydro-4-methoxy-5-methyl-2-(1-methyl-1,3,5-heptatrienyl)-2H-pyran-3-yl ester, isomer A, or a pharmaceutically acceptable salt thereof.

10. A compound of claim 1, (Aminomethyl)phosphonic acid, ethyl[2S-[2α-(E,E,E), 3β,4α,5α]]-tetrahydro-4-methoxy-5-methyl-2-(1-methyl-1,3,5-heptatrienyl)-2H-pyran-3-yl ester, isomer B, or a pharmaceutically acceptable salt thereof.

* * * * *

UNITED STATES PATENT AND TRADEMARK OFFICE
CERTIFICATE OF CORRECTION

PATENT NO. : 5,248,790
DATED : September 28, 1993
INVENTOR(S) : Uwe D. Treuner

It is certified that error appears in the above-identified patent and that said Letters Patent is hereby corrected as shown below:

Column 20, line 68, after the words "(1-methyl-", insert -- 1,3,5-heptatrienyl)- --.

Signed and Sealed this

Twenty-ninth Day of March, 1994

Attest:

BRUCE LEHMAN

*Attesting Officer*  *Commissioner of Patents and Trademarks*